United States Patent [19]

Nakai et al.

[11] Patent Number: 5,126,482
[45] Date of Patent: Jun. 30, 1992

[54] PROCESS FOR PRODUCING FLUORINE-CONTAINING CARBOXYLIC ACIDS

[75] Inventors: Takeshi Nakai, Kanagawa; Osamu Takahashi, Saitama, both of Japan

[73] Assignee: Nippon Mining Co., Ltd., Tokyo, Japan

[21] Appl. No.: 636,002

[22] Filed: Jan. 3, 1991

Related U.S. Application Data

[62] Division of Ser. No. 378,556, Jul. 10, 1989, abandoned.

[30] Foreign Application Priority Data

| Jul. 8, 1988 [JP] | Japan | 1-168814 |
| Oct. 17, 1988 [JP] | Japan | 1-259363 |
| Jan. 30, 1989 [JP] | Japan | 1-17560 |
| Jan. 30, 1989 [JP] | Japan | 64-17561 |

[51] Int. Cl.$^5$ ............................................ C07C 51/08
[52] U.S. Cl. ............................... 554/150; 560/145; 560/219; 560/227; 562/605; 562/840; 562/857; 562/598; 562/861; 562/864; 568/842; 554/223
[58] Field of Search ................ 562/598; 260/405.5, 260/408

[56] References Cited

U.S. PATENT DOCUMENTS

| 2,594,570 | 4/1952 | Linn | 562/598 X |
| 2,761,875 | 9/1956 | Stoner | 562/598 |
| 4,112,225 | 9/1978 | Holland et al. | 560/61 X |
| 4,966,996 | 10/1990 | Schäfer | 562/598 |

OTHER PUBLICATIONS

*Tetrahedron*, vol. 37, pp. 2249-2254, (1984).
*Tetrahedron Letters* vol. 25, No. 36, pp. 3987-3990, (1984).
*Tetrahedron Letters*, vol. 25, No. 36, pp. 3991-3994, (1984).
*Patent Abstracts of Japan*, vol. 7, No. 273 (C-198) (1418), Dec. 6, 1983; abstract of JP-A-58 152 830, (Daikin Kogyo), Oct. 9, 1983.
*Chemical Abstracts*, vol. 100, No. 1, Jan. 2, 1984, 5880E.
*Chemical Abstracts*, vol. 93, 1980, p. 650, 25870s and p. 854, 45853s.

Primary Examiner—Jose G. Dees
Assistant Examiner—Vera C. Clarke
Attorney, Agent, or Firm—Sughrue, Mion, Zinn, Macpeak & Seas

[57] ABSTRACT

Novel fluorine-containing compounds and processes for producing the same are disclosed, the compounds being represented by the general formula (I):

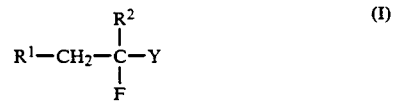

wherein $R^1$ represents an alkyl group or an alkylvinyl group; $R^2$ represents a fluoroalkyl group; and Y represents a carboxyl group, a chloroformyl group, an alkoxyalkoxycarbonyl group or a hydroxymethyl group.

4 Claims, No Drawings

PROCESS FOR PRODUCING FLUORINE-CONTAINING CARBOXYLIC ACIDS

This is a divisional of application Ser. No. 07/378,556 filed Jul. 10, 1989, now abandoned.

BACKGROUND OF THE INVENTION

This invention relates to novel fluorine-containing compounds which are useful as intermediates for functional materials such as medicines, agricultural chemicals and liquid crystal compounds, and also relates to a process for producing the novel compounds.

In general, many of the fluorine-containing compounds have unique physical properties and/or physiological activities, and many studies of the syntheses of fluorine-containing compounds have so far been conducted (see, for example, "Biomedicinal Aspects of Fluorine Chemistry", edited by R. Filler and Y. Kobayashi, Kodansha Ltd., Tokyo and Elsevier Biomedical, Amsterdam, 1982).

However, a compound represented by the following general formula (I) has not yet been known:

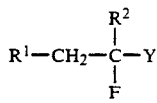
(I)

wherein $R^1$ represents an alkyl group or an alkylvinyl group; $R^2$ represents a fluoroalkyl group; and Y represents a carboxyl group, a chloroformyl group, an alkoxycarbonyl group or a hydroxymethyl group.

The present invention has been made under these circumstances. It is, therefore, an object of the present invention to provide novel fluorine-containing compounds, especially in optically active forms, which are useful as intermediates for functional materials such as medicines, agricultural chemicals and liquid crystal compounds and for other compounds. It is another object of the invention to provide a process for the production of the novel compounds.

The foregoing and other objects, features and advantages of the present invention will be apparent from the detailed description given below and the appended claims.

SUMMARY OF THE INVENTION

In one aspect of this invention, there are provided novel fluorine-containing compounds represented by the general formula (I):

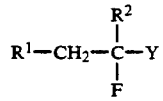
(I)

wherein $R^1$ represents an alkyl group or an alkylvinyl group; $R^2$ represents a fluoroalkyl group; and Y represents a carboxyl group, a chloroformyl group, an alkoxyalkoxycarbonyl group or a hydroxymethyl group), and also provided are the above compounds in optically active forms.

In other aspects of the invention, there are provided a process for producing a fluorine-containing carboxylic acid represented by the general formula (V)

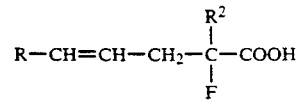
(V)

(wherein R represents a hydrogen atom or an alkyl group, and $R^2$ are as defined above), which comprises reacting an allyl ester of a fluorine-containing carboxylic acid, the allyl ester being represented by the general formula (II)

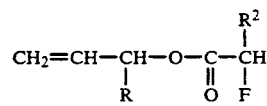
(II)

(wherein R and $R^2$ are as defined above) with a tertiary amine represented by the general formula (III)

(wherein $R^3$, $R^4$ and $R^5$ are the same or different and each independently represent an alkyl group, and may be bonded with each other to form a ring) and a silyl triflate represented by the general formula (IV)

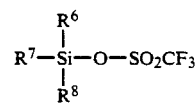
(IV)

(wherein $R^6$, $R^7$ and $R^8$ are the same or different and each independently represent an alkyl group or an aryl group); a process for preparing a fluorine-containing carboxylic acid represented by the general formula (VI)

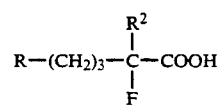
(VI)

(wherein R and $R^2$ are as defined above) which comprises hydrogenating a fluorine-containing carboxylic acid represented by the above-mentioned general formula (V); a process for preparing a fluorine-containing carboxylic acid chloride represented by the general formula (VII)

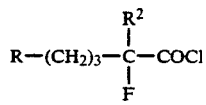
(VII)

(wherein R and $R^2$ are as defined above) which comprises reacting a fluorine-containing carboxylic acid represented by the above-mentioned general formula (VI) with a chlorinating agent; a process for preparing a fluorine-containing carboxylic acid ester represented by the general formula (VIII)

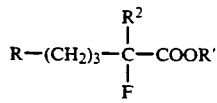

(wherein R' represents an alkyl group or an aryl group, and R and $R^2$ are as defined above) which comprises reacting a fluorine-containing carboxylic acid chloride represented by the above-mentioned general formula (VII) with an alcohol or a phenol; and a process for preparing a fluorine-containing alcohol represented by the general formula (X)

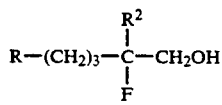

(wherein R and $R^2$ are as defined above) which comprises reacting a fluorine-containing compound represented by the general formula (IX)

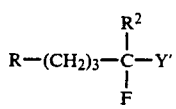

(wherein R and $R^2$ are as defined above, and Y' represents a carboxyl group, a chloroformyl group or an alkoxycarbonyl group) with a metal hydride.

DETAILED DESCRIPTION OF THE INVENTION

As examples of the compound of the present invention represented by the general formula (I), there may be mentioned 2-fluoro-2-(trifluoromethyl)-4-hexenoic acid, 2-fluoro-2-(trifluoromethyl)-4-heptenoic acid, 2-fluoro-2-(trifluoromethyl)-4-octenoic acid, 2-fluoro-2-(trifluoromethyl)-4-nonenoic acid, 2-fluoro-2-(trifluoromethyl)-4-decenoic acid, 2-fluoro-2-(trifluoromethyl)-4-undecenoic acid, 2-fluoro-2-(trifluoromethyl)-4-dodecenoic acid, 2-fluoro-2-( trifluoromethyl)hexanoic acid, 2-fluoro-2-(trifluoromethyl)heptanoic acid, 2-fluoro-2-(trifluoromethyl)octanoic acid, 2-fluoro-2-(trifluoromethyl)nonanoic acid, 2-fluoro-2-(trifluoromethyl)decanoic acid , 2-fluoro-2-(trifluoromethyl)undecanoic acid, 2-fluoro-2-(trifluoromethyl)dodecanoic acid, 2-fluoro-2-(trifluoromethyl)hexanoyl chloride, 2-fluoro-2-(trifluoromethyl)heptanoyl chloride, 2-fluoro-2-(trifluoromethyl)octanoyl chloride, 2-fluoro-2-(trifluoromethyl)nonanoyl chloride, 2-fluoro-2-(trifluoromethyl)decanoyl chloride, 2-fluoro-2-(trifluoromethyl)undecanoyl chloride, 2-fluoro-2-(trifluoromethyl)dodecanoyl chloride, methyl 2-fluoro-2-(trifluoromethyl)hexanoate, ethyl 2-fluoro-2-(trifluoromethyl)hexanoate, isopropyl 2-fluoro-2-(trifluoromethyl)hexanoate, pentyl 2-fluoro-2-(trifluoromethyl)hexanoate, methyl 2-fluoro-2-(trifluoromethyl)heptanoate, ethyl 2-fluoro-2-(trifluoromethyl)heptanoate, isopropyl 2-fluoro-2-(trifluoromethyl)heptanoate, pentyl 2-fluoro-2-(trifluoromethyl)heptanoate, methyl 2-fluoro-2-(trifluoromethyl)octanoate, ethyl 2-fluoro-2-(trifluoromethyl)octanoate, isopropyl 2-fluoro-2-(trifluoromethyl)octanoate, pentyl 2-fluoro-2-(trifluoromethyl)octanoate, methyl 2-fluoro-2-(trifluoromethyl)nonanoate, ethyl 2-fluoro-2-(trifluoromethyl)nonanoate, isopropyl 2-fluoro-2-(trifluoromethyl)nonanoate, pentyl 2-fluoro-2-(trifluoromethyl)nonanoate, methyl 2-fluoro-2-(trifluoromethyl)decanoate, ethyl 2-fluoro-2-(trifluoromethyl)decanoate, isopropyl 2-fluoro-2-(trifluoromethyl)decanoate, pentyl 2-fluoro-2-(trifluoromethyl)decanoate, methyl 2-fluoro-2-(trifluoromethyl)undecanoate, ethyl 2-fluoro-2-(trifluoromethyl)undecanoate, isopropyl 2-fluoro-2-(trifluoromethyl)undecanoate, pentyl 2-fluoro-2-(trifluoromethyl)undecanoate, methyl 2-fluoro-2-(trifluoromethyl)dodecanoate, ethyl 2-fluoro-2-(trifluoromethyl)dodecanoate, isopropyl 2-fluoro-2-(trifluoromethyl)-dodecanoate, pentyl 2-fluoro-2-(trifluoromethyl)dodecanoate, 2-fluoro-2-(trifluoromethyl)-1-hexanol, 2-fluoro-2-(trifluoromethyl)-1-heptanol, 2-fluoro-2-(trifluoromethyl)-1-octanol, 2-fluoro-2-(trifluoromethyl)-1-nonanol, 2-fluoro-2-(trifluoromethyl)-1-decanol, 2-fluoro-2-(trifluoromethyl)-1-undecanol and 2-fluoro-2-(trifluoromethyl)-1-dodecanol.

In the above-mentioned general formula (I), the alkyl groups represented by $R^1$ and $R^2$ are not especially limited, but it is preferable that these alkyl groups each have 2 to 9 carbon atoms from the practical viewpoint. The compounds of the general formula (I) according to the present invention include optically active forms. These optically active forms can be utilized especially as intermediate materials for the syntheses of medicines having excellent physiological activity, agricultural chemicals, ferroelectric liquid crystal compounds and others.

Representative examples of the compound of the above-mentioned general formula (I) will be described below with respect to physical properties:

(S)-(+)-2-Fluoro-2-(Trifluoromethyl)-4-Hexenoic Acid 1. boiling point: 150° C./25 mmHg (Kugelrohr)
2. $^1H$ NMR (CDCl$_3$): 1.70(3H,d,J=6.0 Hz), 2.65–3.25(2H,m), 5.25–6.05(2H,m), 11.95(OH,s)
3. $^{19}F$ NMR (CDCl$_3$, external standard CF$_3$CO$_2$H) −0.6(3F,d,$J_{FF}$=6.2 Hz), 95.3(1F,m)
4. $^{13}C$ NMR (CDCl$_3$): 17.9(C6), 34.9(C3,d,$J_{HF}$=21 Hz), 93.8(C2,dq,$J_{CF}$=202 Hz, 31 Hz), 119.5(C4,d,$J_{CF}$=4 Hz), 121.7(CF$_3$,dq,$J_{CF}$=28 Hz, 286 Hz), 133.8(C5), 170.3(C1,d,$J_{CF}$=26 Hz)
5. $[\alpha]_D^{25}$: +4.74° (c1.0,CHCl$_3$)

2-Fluoro-2-(Trifluoromethyl)-4-Decenoic Acid $^{19}F$ NMR (CDCl$_3$, external standard CF$_3$CO$_2$H): −0.8(3F,d,$J_{FF}$=6.5 Hz), 96.0(1F,m)

(S)-(−)-2-Fluoro-2-(Trifluoromethyl)Hexanoic Acid 1. boiling point: 85°–92° C./15 mmHg
2. $^1H$ NMR (CDCl$_3$): 1.00(3H,bt), 1.1–1.7(4H,m), 1.8–2.6(2H,m), 10.10(OH,b)
3. $^{19}F$ NMR (CDCl$_3$, external standard CF$_3$CO$_2$H): −0.25(3F,d,5.6 Hz), 96.0(1F,m)
4. $^{13}C$ NMR (CDCl3): 13.3(C6), 22.2(C5), 24.0(C4,d,$J_{CF}$=2.0 Hz), 30.5(C3, d,$J_{CF}$=20.9 Hz), 94.1(C2,dq,$J_{CH}$=119.4 Hz, 31.2 Hz), 121.4(CF$_3$,dq,$J_{CF}$=28.7 Hz, 284.3 Hz), 169.0(C1,d,$J_{CH}$=26.5 Hz)
5. $[\alpha]_D^{25}$: −4.42° (cl.7,CHCl$_3$), 93%ee (R)-(+)-2-Fluoro-2-(Trifluoromethyl)Decanoic Acid 1. $^1H$ NMR (CDCl$_3$): 0.90(3H,bt), 1.1–1.7(12H,m), 1.8–2.6(2H,m), 9.35(OH,b)

2. $^{19}F$ NMR (CDCl$_3$, external standard CF$_3$CO$_2$H): $-0.40$(3F,d,5.6 Hz), $+96$(1F,m)

3. $\alpha_D^{25}$: $+0.111°$ (neat, $l=1.0$), 86%ee (R)-(−)-2-Fluoro-2-(Trifluoromethyl)Hexanoyl Chloride 1. boiling point: 40°–60° C./150 mmHg
2. $^1H$ NMR (CDCl$_3$): 0.95(3H,t,7.1Hz), 1.1–1.8(4H,m), 2.0–2.7(2H,m)
3. $^{19}F$ NMR (CDCl$_3$, external standard CF$_3$CO$_2$H): $-1.17$(3F,d,5.6 Hz), 83.0(1F,m)
4. $^{13}C$ NMR (CDCl3): 13.6(C6), 22.6(C5), 24.3(C4,d,$J_{CH}=2.6$ Hz): 31.5(C3,d,$J_{CH}=21.0$ Hz), 97.5(C2,dq,$J_{CF}=210.8$ Hz, 31.2 Hz), 121.4(CF$_3$,dq,$J_{CF}=29.3$ Hz, 285.3 Hz), 170.4(C1,d,$J_{CF}=33.9$ Hz)
5. $\alpha_D^{25}$: $-1.44°$ (neat, $l=1.0$ cm), 93%ee (S)-(+)-2-Fluoro-2-(Trifluoromethyl)Decanoyl Chloride 1. boiling point: 62° C./3 mmHg
2. $^1H$ NMR (CDCl$_3$): 0.90(3H,6t), 1.1–1.8(14H,m), 2.0–2.7(2H,m)
3. $^{19}F$ NMR (CDCl$_3$, external standard CF$_3$CO$_2$H): $-1.3$(3F,d,5.6 Hz), $+83$(1F,m)
4. $[\alpha]_D^{25}$: $+0.770°$ (neat, $l=1.0$ cm)

Methyl (S)-(−)-2-Fluoro-2-(Trifluoromethyl)Hexanoate 1. boiling point: 100°–140° C. (Kugelrohr)
2. $^1H$ NMR (CDCl$_3$): 0.93(3H,t,7.0 Hz), 1.1–1.6(4H,m), 1.9–2.3(2H,m), 3.90(3H,s)
3. $^{19}F$ NMR (CDCl$_3$, external standard CF$_3$CO$_2$H): $-0.25$(3F,d,5.6 Hz), 96(1F,m)
4. $^{13}C$ NMR (CDCl$_3$): 13.7(C6), 22.4(C5), 24.3(C4,d,$J_{CH}=2.4$ Hz), 30.9(C3,d,$J_{CH}=21.4$ Hz), 53.6(OCH$_3$), 94.3(C2,dq,$J_{CH}=201.6$ Hz, 31.6 Hz), 122.0(CF$_3$,dq,$J_{CH}=28.6$ Hz, 286.0 Hz), 165.7(C1,$J_{CF}=25.0$ Hz)
5. $[\alpha]_D^{25}$: $-6.5°$ (c0.3, CHCl$_3$)

(S)-(+)-2-Fluoro-2-(Trifluoromethyl)-1-Hexanol 1. boiling point: 150°–155° C.
2. $^1H$ NMR (CDCl$_3$): 0.94(3H,t,6.9 Hz), 1.3–1.6(4H,m), 1.8–2.1(2H,m), 2.69(OH,s), 3.88(2H,d,18.0 Hz)
3. $^{19}F$ NMR (CDCl$_3$, external standard CF$_3$CO$_2$H): 0.05(3F,d,5.6 Hz), 97(1F,m)
4. $^{13}C$ NMR (CDCl$_3$): 13.8(C6), 23.1(C5), 24.4(C4,d,$J_{CF}=5.5$ Hz), 29.5(C3,d,$J_{CF}=21.1$ Hz), 61.5(C1,d,$J_{CF}=25.5$ Hz), 95.3(C2,dq,$J_{CH}=185.3$ Hz, 28.8 Hz), 124.3(CF$_3$,dq,$J_{CF}=28.6$ Hz, 286.1 Hz)
5. $\alpha_D^{25}$: $+0.050°$ (neat, $l=1.0$ cm)

(R)-(−)-2-Fluoro-2-(Trifluoromethyl)-1-Decanol 1. boiling point: 88° C./3 mmHg
2. $^1H$ NMR (CDCl$_3$): 0.90(3H,bt), 1.3–2.3(15H, m), 3.88(2H,d,18 Hz)
3. $^{19}F$ NMR (CDCl$_3$, external standard CF$_3$CO$_2$H): $+0.10$(3F,d,5.6 Hz), $+98$(1F,m)
4. $[\alpha]_D^{25}$: $-1.94°$ (c5.7,CHCl$_3$)

Of the compounds represented by the above-mentioned general formula (I), the fluorine-containing carboxylic acid compound in which $R^1$ is an alkylvinyl group and Y is a carboxyl group, i.e., the fluorine-containing carboxylic acid of the above-mentioned formula (V), may be synthesized from a fluorine-containing carboxylic acid allyl ester, as a starting material, represented by the above-mentioned general formula (II).

In the general formula (II), the alkyl groups represented by R is not especially limited, but it is preferable that the alkyl group has 2 to 9 carbon atoms from the practical viewpoint.

As this fluorine-containing carboxylic acid allyl ester, there may be employed, for example, a 3-buten-2-yl, 1-penten-3-yl, 1-hexen-3-yl, 1-octen-3-yl or 1-decen-3-yl ester of a fluorine-containing carboxylic acid such as 2,3,3,3-tetrafluoropropionic acid.

That is, the fluorine-containing carboxylic acid of general formula (V) may be obtained by reacting a starting material represented by the general formula (II) with a tertiary amine represented by the above-mentioned general formula (III) and a silyl triflate represented by the above-mentioned general formula (IV). As this tertiary amine, there may be employed, for example, trimethylamine, triethylamine, dicyclohexylmethylamine, diisopropylethylamine or N-ethylpiperidine. As the silyl triflate represented by the general formula (IV), there may be employed, for example, trimethylsilyl triflate, t-butyldimethylsilyl triflate, triethylsilyl triflate, dimethylthexylsilyl triflate or methyldiphenylsilyl triflate.

The above reaction can be performed very easily by mixing the compounds represented by the above-mentioned general formulae (II), (III) and (IV) in a solvent of the ether type or the halogenated hydrocarbon type. After completion of the reaction, a diluted acid or an aqueous alkaline solution is added to the reaction mixture and then the resulting mixture is subjected to ordinary treatments such as extraction, drying, concentration, etc., whereby a fluorine-containing carboxylic acid represented by the general formula (V) can be obtained.

In performing the above reaction, it is preferable that the tertiary amine and the silyl triflate are used in an amount about 1.1 to 5 equivalent to the allyl ester. The reaction temperature may suitably be selected from the range of from about 0° to 30° C. Preferably employed as the solvent is an ether type solvent such as diethyl ether or dimethoxyethane, or a halogenated hydrocarbon type solvent such as dichloromethane, chloroform or trichloroethane.

In order to obtain an optically active fluorine-containing carboxylic acid represented by the general formula (V) through the above reaction, there may be employed a method in which the absolute configuration of the R-bonded carbon atom in the compound of general formula (II) is arranged beforehand so as to be either R or S. For doing this, an optically active allyl alcohol which is relatively easily available may be converted into an ester of a fluorine-containing carboxylic acid according to a generally employed esterification technique. In this case, the fluorine-containing carboxylic acid need not be optically active.

A fluorine-containing carboxylic acid represented by the above-mentioned formula (VI) can be obtained by catalytic hydrogenation of the compound represented by the above-mentioned formula (V). No racemization occurs when an optically active compound is employed as a raw material. The compound represented by the above-mentioned formula (V) is dissolved in an organic solvent, subsequently palladium on activated carbon, platinum oxide or the like is added thereto as a catalyst, and then the resulting mixture is stirred under a hydrogen atmosphere at a temperature in the range of from 0° C. to the boiling point of the solvent. As the reaction solvent, there may be employed, for example, ether, pentane, hexane, ethanol or ethyl acetate, but preferred of these is ether because of the easy separation from the product. Further, a preferred hydrogen pressure is in the range of from the atmospheric pressure to a slightly higher pressure from the viewpoint of reaction operation.

The fluorine-containing carboxylic acid chloride represented by the above-mentioned formula (VII) may be prepared by reacting the compound represented by the above-mentioned formula (VI) with a chlorinating agent such as phthalyl chloride, phosphorus pentachloride, phosphorus trichloride or thionyl chloride, followed by fractional distillation. According to this method, even when an optically active compound has been used as a raw material, there can be obtained an optically active product without recemization. For this reaction, the amount of the chlorinating agent is preferably from 1 to 10 equivalent to the compound of formula (VI), and the reaction temperature may suitably be selected from the range of from 20° to 110° C. As a solvent, benzene, toluene, chloroform or the like can be used. Alternatively, an excess of the chlorinating agent may be used as a solvent. It is particularly preferred to employ phthalyl chloride as both a chlorinating agent and a solvent.

The fluorine-containing carboxylic acid ester represented by the above-mentioned formula (VIII) may be obtained by reacting the compound represented by the above-mentioned formula (VII) with an alcohol (1 to 20 equivalent).

This alcohol is not especially limited, but it is preferable that the alcohol has 1 to 10 carbon atoms from the practical viewpoint.

No racemization occurs when an optically active compound has been used as a raw material. As a solvent for this reaction, dichloromethane, chloroform, pyridine or the like may be used, but the reaction may also be performed without a solvent. The reaction temperature may suitably be selected from the range of from $-10°$ to 50° C. An ester with a lower alcohol can also be obtained by reacting the compound represented by the formula (VI) with a large excess of the alcohol in the presence of an acid catalyst, but difficulties are encountered to isolate the product which is highly volatile.

The fluorine-containing alcohol represented by the above-mentioned formula (X) may be obtained by reducing any of the compounds represented by the above-mentioned formulae (VI) to (VIII) with 1 to 20 equivalent of a metal hydride. No racemization occurs when an optically active compound has been used as a raw material. As the metal hydride to be used in this reaction, there may be employed, for example, lithium aluminum hydride, diisobutylaluminum hydride or sodium boron hydride. As a reaction solvent, ether, dimethoxyethane, tetrahydrofuran, toluene or the like may preferably be used. It is particularly preferred to perform the above reaction in an ether solvent using lithium aluminum hydride as a reducing agent. The reaction temperature may suitably be selected from the range of from $-10°$ C. to the boiling point of the medium.

The novel compounds of the present invention are useful as intermediates for functional materials such as medicines, agricultural chemicals and liquid crystal compounds and for other compounds, and the processes of this invention for producing these compounds can be easily practiced under mild conditions. Furthermore, by the use of optically active allyl alcohols which are readily available, the compounds of the invention can be obtained in optically active forms with great ease.

The present invention will be illustrated in more detail with reference to the following examples, which should not be construed to be limiting the scope of the invention.

REFERENCE EXAMPLE 1

In 20 ml of dichloromethane were dissolved 0.72 g of (S)-(−)-3-buten-2-ol (98%ee) and 0.95 g of pyridine, and then 1.65 g of 2,3,3,3-tetrafluoropropionyl chloride was dropwise added to the above-obtained solution while the solution was being cooled with ice. The resulting mixture was stirred at room temperature for 30 minutes, subsequently water was added thereto, and then the reaction mixture was subjected to extraction with ether. The resulting extract was washed with 1N hydrochloric acid, a 5% aqueous solution of sodium hydrogencarbonate, and brine, and then dried with magnesium sulfate. Subsequently, the solvent was removed under reduced pressure, and the residual product was distilled, thereby obtaining 1.50 g of 3-buten-2-yl 2,3,3,3-tetrafluoropropionate having the following physical properties.

1. Boiling point: 65° C./60 mmHg
2. $^1$H NMR (CDCl$_3$): 1.41(3H,d,J=6.0 Hz), 5.25(1H,dq,J=68.4 Hz,6.5 Hz), 5.20–6.15(4H,m)
3. $^{19}$F NMR (CDCl$_3$, external standard CF$_3$CO$_2$H) −2.0(3F,dd, J=10.3 Hz, J=6.4 Hz), 123(1F,dq, J=38.9 Hz, J=10.3 Hz)

EXAMPLE 1

In 1 ml of dichloromethane was dissolved 0.18 g of 3-buten-2-yl 2,3,3,3-tetrafluoropropionate as obtained in Reference Example 1, and the resulting solution was cooled with ice under a nitrogen atmosphere. Thereto were added 0.29 g of trimethylsilyl triflate and 0.21 g of triethylamine, and the resulting mixture was stirred at room temperature for 36 hours. Then, the reaction mixture was poured into a 5% aqueous solution of potassium carbonate, and the aqueous layer was washed with ether. The resulting aqueous layer was acidified with concentrated hydrochloric acid, and then extracted with dichloromethane. The resulting extract was dried with magnesium sulfate, and the solvent was removed under reduced pressure. Subsequently, the residual product was distilled to obtain 0.14 g of (S)-(+)-2-fluoro-2-(trifluoromethyl)-4-hexenoic acid having the physical properties as mentioned hereinbefore.

The geometrical configuration of this compound was examined by means of $^{13}$C NMR, and was found to be 100%E.

Subsequently, 78 mg of this (S)-(+)-2-fluoro-2-(trifluoromethyl)-4-hexenoic acid and 0.03 ml of pyridine were dissolved in 1 ml of acetonitrile, and then 0.10 g of N,N'-disuccinimidyl carbonate was added to the above-obtained solution at 0° C. The resulting mixture was stirred at room temperature for 2 hours, subsequently 0.06 ml of (S)-(−)-α-phenylethylamine was added thereto, and then the mixture was stirred at room temperature for 2 hours. The reaction mixture thus obtained was diluted with ether, washed with 1N hydrochloric acid, a 5% aqueous solution of sodium hydrogencarbonate, and brine, and then dried with magnesium sulfate. Subsequently, the solvent was removed under reduced pressure, and the residual product was analyzed by means of liquid chromatography. As a result, the above-obtained (S)-(+)-2-fluoro-2-(trifluoromethyl)-4-hexenoic acid had an optical purity of 92%ee.

REFERENCE EXAMPLE 2

In 200 ml of dichloromethane were dissolved 28 g (0.22 mol) of (R)-(−)-1-octen-3-ol (92%ee) and 21 ml (0.26 mol) of pyridine, and then 39.5 g (0.24 mol) of 2,3,3,3-tetrafluoropropionyl chloride was dropwise added to the above-obtained solution while the solution was being cooled with ice. The resulting mixture was stirred at room temperature for 1 hour, subsequently water was added thereto, and then the reaction mixture was subjected to extraction with ether. The resulting extract was washed with 1N hydrochloric acid, a 5% aqueous solution of sodium hydrogencarbonate, and brine, and then dried with magnesium sulfate. Subsequently, the solvent was removed under reduced pressure, and the residual product was distilled at 95° C. under 25 mmHg, thereby obtaining 42.3 g of 1-octen-3-yl 2,3,3,3-tetrafluoropropionate in a yield of 76%.

EXAMPLE 2

In 150 ml of dichloromethane was dissolved 42 g (0.16 mol) of the 1-octen-3-yl 2,3,3,3-tetrafluoropropionate as obtained in Reference Example 2, and the resulting solution was cooled with ice under a nitrogen atmosphere. Thereto were added 40 ml (0.2 mol) of trimethylsilyl triflate and 29 ml (0.2 mol) of triethylamine, and the resulting mixture was stirred at room temperature for 120 hours. Then, the reaction mixture was diluted with hexane, and then subjected to extraction with a 7.5% aqueous solution of sodium hydroxide. The resulting aqueous extract was acidified with concentrated hydrochloric acid, and then extracted again with dichloromethane. The resulting extract was dried with magnesium sulfate, and the solvent was removed under reduced pressure, thereby obtaining 37 g of (+)-2-fluoro-2-(trifluoromethyl)-4-decenoic acid in a yield of 88%.

EXAMPLE 3

In 100 ml of ether was dissolved 19.0 g of (S)-(+)-2-fluoro-2-(trifluoromethyl)-4-hexenoic acid, and 3 g of activated carbon having 5% palladium supported thereon was added to the above-obtained solution. Subsequently, the resulting mixture was vigorously stirred under an atmospheric-pressure hydrogen atmosphere at 0° C. for 5 hours, and then at room temperature for 15 hours. Thereafter, the reaction mixture was filtered through Celite, and the solvent was removed from the filtrate under reduced pressure, thereby obtaining 19.0 g of a crude product containing (S)-(−)-2-fluoro-2-(trifluoromethyl)hexanoic acid. Part of this product was distilled under reduced pressure, and the thus-purified product was examined for its properties. As a result, the product was found to have the physical properties as mentioned hereinbefore.

EXAMPLE 4

A mixture of 8.0 g of (S)-(−)-2-fluoro-2-(trifluoromethyl)hexanoic acid and 24.0 g of phthalyl chloride was stirred at 80° C. for 24 hours. Subsequently, the reaction mixture was distilled under reduced pressure, thereby obtaining 8.2 g of (R)-(−)-2-fluoro-2-(trifluoromethyl)hexanoyl chloride having the physical properties as mentioned hereinbefore.

REFERENCE EXAMPLE 3

In 2 ml of pyridine was dissolved 0.05 g of (S)-(−)-1-phenylethylamine. To this solution was added 0.05 g of the (R)-(−)-2-fluoro-2-(trifluoromethyl)hexanoyl chloride as obtained in Example 4, and the resulting mixture was stirred at room temperature for 10 minutes. This reaction mixture was diluted with ether, and subsequently washed with 1N hydrochloric acid, 5% aqueous sodium hydrogencarbonate solution, and then brine. Thereafter, the resulting ether solution was dried with magnesium sulfate and then concentrated, and the resulting product was analyzed by means of liquid chromatography. As a result, the optical purity of the compound obtained in Example 4 was found to be 93%ee.

EXAMPLE 5

To 0.5 ml of methanol was added 0.17 g of (R)-(−)-2-fluoro-2-(trifluoromethyl)hexanoyl chloride, and this mixture was stirred at room temperature for 30 minutes. The resulting reaction mixture was distilled with Kugelrohr under atomspheric pressure, thereby obtaining 0.15 g of methyl (S)-(−)-2-fluoro-2-(trifluoromethyl)hexanoate having the physical properties as mentioned hereinbefore.

EXAMPLE 6

In 80 ml of anhydrous ether was dissolved 7.30 g of (R)-(−)-2-fluoro-2-(trifluoromethyl)hexanoylchloride, and then 0.83 g of lithium aluminum hydride was portionwise added to the above-obtained solution while the solution was being cooled with ice. The resulting mixture was stirred for 30 minutes. Thereafter, 1N hydrochloric acid was portionwise added to the resulting reaction mixture while the mixture was being cooled with ice, and then a reaction product was extracted with ether. The resulting organic layer was dried with magnesium sulfate, the solvent was removed under reduced pressure, and then the residual product was distilled. Thus, 4.6 g of (S)-(+)-2-fluoro-2-(trifluoromethyl)-1-hexanol was obtained which had the physical properties as mentioned hereinbefore.

EXAMPLE 7

In 2 ml of ether was dissolved 0.15 g of methyl (S)-(−)-2-fluoro-2-(trifluoromethyl)hexanoate, and then 0.06 g of lithium aluminum hydride was added to the above-obtained solution while the solution was being cooled with ice. The resulting mixture was stirred at room temperature for 40 minutes, subsequently diluted hydrochloric acid was added to the reaction mixture, and then the resulting organic layer was analyzed by means of gas chromatography (SE-30, 2 m, 50° C.). The result was compared with that for the product as obtained in Example 6, and it was found that 2-fluoro-2-(trifluoromethyl)-1-hexanol had been formed quantitatively.

EXAMPLE 8

In 120 ml of ether was dissolved 10 g (39 mmol) of (R)-2-fluoro-2-(trifluoromethyl)-4-decenoic acid, and 3 g of activated carbon having 5% palladium supported thereon was added to the above-obtained solution. The resulting mixture was vigorously stirred under an atmospheric-pressure hydrogen atmosphere for 96 hours. Subsequently, the reaction mixture was filtered through Celite, and the solvent was removed under reduced pressure, thereby obtaining 8.5 g of (R)-(+)-2-fluoro-2-

(trifluoromethyl)decanoic acid having the physical properties as mentioned hereinbefore, in a yield of 85%.

EXAMPLE 9

2.0 g (7.7 mmol) of (R)-(+)-2-fluoro-2-(trifluoromethyl)-decanoic acid was cooled with ice, and 1.8 g (8.5 mmol) of phosphorus pentachloride was added to the acid. The resulting mixture was stirred for 30 minutes while being cooled with ice, and then stirred at room temperature for 8 hours. Subsequently, the resulting reaction mixture was distilled under reduced pressure, thereby obtaining 1.4 g of (S)-(+)-2-fluoro-2-(trifluoromethyl)decanoyl chloride having the physical properties as mentioned hereinbefore, in a yield of 66%.

EXAMPLE 10

In 10 ml of anhydrous ether was dissolved 1.4 g (5.1 mmol) of (S)-(+)-2-fluoro-2-(trifluoromethyl)decanoyl chloride, and then 0.14 g (3.5 mmol) of lithium aluminum hydride was portion-wise added to the above-obtained solution while the solution was being cooled with ice. The resulting mixture was stirred for 3 hours. Thereafter, 1N hydrochloric acid was portionwise added to the resulting reaction mixture while the mixture was being cooled with ice, and then a reaction product was extracted with ether. The resulting ether layer was dried with magnesium sulfate, the solvent was removed under reduced pressure, and then the residual product was distilled. Thus, there was obtained 0.69 g of (R)-(−)-2-fluoro-2-(trifluoromethyl)-1-decanol having the physical properties as mentioned hereinbefore, in a yield of 56%.

While the invention has been described in detail and with reference to specific embodiments thereof, it will be apparent to one skilled in the art that various changes and modifications can be made therein without departing from the spirit and scope thereof.

What is claimed is:

1. A process for producing a fluorine-containing carboxylic acid represented by the formula (V):

$$R-CH=CH-CH_2-\underset{\underset{F}{|}}{\overset{\overset{R^2}{|}}{C}}-COOH \quad (V)$$

wherein R represents a hydrogen atom or an alkyl group; and $R^2$ represents a fluoroalkyl group, which comprises (i) reacting an allyl ester of a fluorine-containing carboxylic acid, said allyl ester being represented by the formula (II):

$$CH_2=CH-\underset{\underset{R}{|}}{CH}-O-\underset{\underset{O}{\overset{\|}{C}}}{C}-\underset{\underset{F}{|}}{\overset{\overset{R^2}{|}}{CH}} \quad (II)$$

wherein R and $R^2$ are as defined above; with a tertiary amine represented the formula (III):

$$\underset{R^5}{\overset{R^3}{\underset{R^4-N}{\diagdown}}} \quad$$

wherein $R^3$, $R^4$ and $R^5$ are the same or different and each independently represent an alkyl group, and may be bonded with each other to form a ring; and a silyl triflate represented by the formula (IV):

$$R^7-\underset{\underset{R^8}{|}}{\overset{\overset{R^6}{|}}{Si}}-O-SO_2CF_3 \quad (IV)$$

wherein $R^6$, $R^7$ and $R^8$ are the same or different and each independently represent an alkyl group or an aryl group, and (ii) acidifying the product of reaction step (i).

2. A process for producing a fluorine-containing carboxylic acid according to claim 1, wherein in the compound represented by the formula (II), the R-bonded carbon atom is of the absolute configuration of either R or S.

3. A process for producing a fluorine-containing carboxylic acid according to claim 1, wherein the reaction step (i) is conducted at a temperature in the range of from about 0° to 30° C.

4. A process for producing a fluorine-containing carboxylic acid according to claim 1, wherein the reaction step (i) is conducted at a temperature in the range of from about 0° to 30° C., and wherein said reaction step (i) is conducted under a nitrogen atmosphere.

* * * * *